United States Patent [19]

Coassin et al.

[11] Patent Number: 5,419,874
[45] Date of Patent: May 30, 1995

[54] SYNTHESIS REACTION COLUMN

[75] Inventors: Peter J. Coassin, San Juan Capistrano; Edward G. Hanna, Yorba Linda; Carlton B. Mc Kinney, Los Angeles; Jang B. Rampal; Glenn C. Sasaki, both of Yorba Linda; Stephen W. Wunderly, Irvine, all of Calif.

[73] Assignee: Beckman Instruments, Inc., Fullerton, Calif.

[21] Appl. No.: 909,552

[22] Filed: Jul. 6, 1992

[51] Int. Cl.$^6$ .............................................. C08F 8/00
[52] U.S. Cl. .................................. 422/134; 422/131; 422/102; 935/88
[58] Field of Search ................. 422/99, 102, 116, 101, 422/131, 134; 435/287, 296, 285, 311; 935/85, 88

[56] References Cited

U.S. PATENT DOCUMENTS

| | | | |
|---|---|---|---|
| 3,886,928 | 6/1975 | Sarstedt | 422/102 |
| 4,810,471 | 3/1989 | Wachob et al. | 422/101 |
| 4,892,710 | 1/1990 | Wong et al. | 422/102 |
| 4,927,605 | 5/1990 | Dorn et al. | 422/102 |
| 5,057,426 | 10/1991 | Henco et al. | 435/270 |
| 5,061,635 | 10/1991 | Shively | 436/164 |
| 5,093,079 | 3/1992 | Bakaitis et al. | 422/102 |
| 5,137,695 | 8/1992 | Rusnak et al. | 422/116 |
| 5,152,965 | 10/1992 | Fisk et al. | 422/102 |
| 5,179,024 | 1/1993 | Dahms | 422/102 |
| 5,186,898 | 2/1993 | Bridgham et al. | 422/102 |
| 5,219,529 | 6/1993 | Ngo et al. | 422/101 |
| 5,252,296 | 10/1993 | Zuckermann et al. | 422/116 |

FOREIGN PATENT DOCUMENTS 57-35707  7/1982  Japan .

OTHER PUBLICATIONS

McMaster-Carr 1991 catalog (2 pages).
Applied Biosystems Inc. Model 391 PCR-Mate EP DNA Synthesizer Customer Installation Guide (5/89).
Pharmacia Gene Assembler ® Plus Owners Manual (1991).
MilliGen/Biosearch Cyclone TM Plus DNA Synthesizer Operator's Manual (1989).
American Biotech Lab article, "A Simple Manual Method for Oligonucleotide Sythesis" by M. E. Schott. pages 20–23 (1985).

Primary Examiner—Robert J. Warden
Assistant Examiner—Theresa T. Snider
Attorney, Agent, or Firm—William H. May; Paul R. Harder; Thomas Schneck

[57] ABSTRACT

The present invention is directed to a synthesis reaction column which can be conveniently implemented in post synthesis procedures. The reaction column is configured to allow easy connection to a syringe and post synthesis reagent container without requiring connection adapters.

In one embodiment, the reaction column configured in the form of a cylindrical column containing the solid-phase support and having a narrow bore tube extending at one end. The tube functions as a piercing tip for accessing a septum sealed vial containing post synthesis reagent. In another embodiment, the reaction column is configured in the form of a cylindrical barrel enclosing the solid-phase support and having a threaded mount at one end. To complement the reaction column for post synthesis procedures, a vial having a complementary threaded mount at the opening is used for containing a reagent. This vial is conveniently threaded onto the end of the barrel without adapters. Consequently, post synthesis procedures can be implemented conveniently. Both embodiments may be conveniently connected to the reagent delivery system in an automated instrument for carrying out synthesis procedures, as well as post synthesis procedures.

17 Claims, 4 Drawing Sheets

SYNTHESIS REACTION COLUMN

BACKGROUND OF THE INVENTION

1. Field of the Invention

The present invention relates to organic synthesis, and more particularly to a device and method for implementing cleavage and deprotection process in solid-phase nucleic acid synthesis.

2. Background of Related Art

Nucleic acid synthesis (generally referred to as "DNA synthesis") is well known. Generally, this is the process of constructing synthetic single-stranded oligonucleotide through linking of nucleotide, the basic building blocks for DNA. DNA synthesis is described generally in U.S. Pat. No. 4,458,066 issued to Caruthers et al, entitled "Process for Preparing Polynucleotides", which is incorporated by reference herein. The process described therein constructs a single-stranded oligonucleotide using one of several approaches in synthesizing DNA, namely the so-called solid-phase phosphoramidite method which generally involves the steps of deblocking/activation, coupling, capping and oxidation in each synthesis cycle for linking a building block on a solid-phase support. Further reference to this process of DNA synthesis may be found in "oligonucleotide Synthesis—A Practical Approach" edited by M. J. Gait, IRL Press, 1984, which is incorporated by reference herein; and in particular Chapter 3 therein entitled "Solid-Phase Synthesis of Oligodeoxyribonucleotide by the Phosphite-Triester Method" written by Tom Atkinson and Michael Smith.

In an automated system, the various steps are carried out by a reagent delivery system which dispenses a number of chemical reagents in a predetermined sequence in a cycle into a synthesis reaction column containing the solid-phase support, according to instructions from the system controller or computer. After the desired number of cycles have been completed, the synthesized oligonucleotide is separated from the reaction column and collected in a vial. This step is generally referred to as "cleavage". The oligonucleotide may further be subject to a step generally referred to as "deprotection" to complete isolation of the oligonucleotide.

The isolation of oligonucleotide involves the treatment of the solid bound oligonucleotide with a cleavage and/or deprotection reagent. Typically, this reagent is concentrated ammonia solution in water but can be other homogeneous or heterogeneous solutions of appropriate bases, alcohols and water. The cleavage and deprotection process is typically performed in two steps. The cleavage of the oligonucleotide is performed at room temperature for approximately one hour before decanting the mixture into a pressure-sealable vessel for extended higher temperature treatment to effect the removal of secondary protecting groups on the synthetic oligonucleotide. This two step process reduces the quantity of support related contaminants in the final isolated product.

In the case of concentrated ammonia-water, the ammonia component is highly volatile and noxious. At room temperature, a saturated solution of ammonia in water rapidly loses concentration and potency. This can lead to less efficient cleavage and deprotection. Spillage and transfer loses also increase with the current industry process standards.

The prior art synthesis reaction column has followed primarily two designs. The first design involves a double female luer in each end of the column. Luer connections always involve excess unused volume which must be filled with chemical during the synthesis and washed away after each step in the synthesis. As a result, this design requires excess chemical in both the synthesis steps and the wash steps. During post synthesis processing, the user is required to withdraw ammonia into one syringe and connect it to the column. Next a second syringe is connected at the opposite end of the column and the ammonia is pushed from one syringe to the other to accomplish cleavage. After completing cleavage the user must again draw all the ammonia into one syringe and then eject the ammonia into a vial which is then sealed and deprotection procedure is then followed. Extensive sample manipulation is thus required in the foregoing process.

A variation to the foregoing process requires using a male-to-male luer for connecting a needle to the synthesis reaction column.

A second type of column design practiced by Pharmacia Co. takes the form of a cassette that mounts between two threaded tube ferrules. This scheme reduces waste volume due to a luer mount but it involves complicated, inconvenient steps to cleave and deprotect the oligonucleotide from the cassette. For example, among other steps, the procedure involves centrifuging the cassette in a tube.

SUMMARY OF THE INVENTION

The present invention is directed to a synthesis reaction column which can be conveniently implemented in post synthesis procedures. The reaction column is configured to allow easy connection to a syringe and post synthesis reagent container without requiring connection adapters.

In a first described embodiment, the reaction column is configured in the form of a cylindrical column containing the solid-phase support and having a hollow needle extending at one end. The needle functions as a piercing tip as well as a tube for connecting to a septum sealed vial containing post synthesis reagent. The column may be interference fitted to a syringe. No adapter is therefore required for connecting the column to access reagents. This embodiment allows convenient implementation of post synthesis procedures as compared to the prior art approaches.

In a second described embodiment, the reaction column is configured in the form of a cylindrical barrel enclosing the solid-phase support and having a threaded mount at one end. The other end of the barrel is adapted for interference fitting to a syringe. To complement the reaction column for post synthesis procedures, a vial having a complementary threaded mount at its opening is used for containing a reagent. This vial is conveniently threaded onto the end of the barrel without adapters. Consequently, post synthesis procedures can be implemented conveniently.

Both embodiments may be conveniently connected to the reagent delivery system in an automated synthesis instrument for carrying out synthesis procedures, as well as post synthesis procedures.

DESCRIPTION OF THE ILLUSTRATED EMBODIMENTS

The following description is of the best contemplated mode of carrying out the invention. This description is made for the purpose of illustrating the general principles of the invention and should not be taken in a limiting sense. The scope of the invention is best determined by reference to the appended claims.

While the present invention is described in the context of nucleic acid synthesis, it is to be understood that the present invention can be implemented for other types of synthesis, e.g. peptide and protein synthesis, or carrying out other types of reactions requiring a solid-phase support in connection with nucleotide chemistry, e.g. fluorescence labelling, post synthesis modifications, etc.

Figure 1:
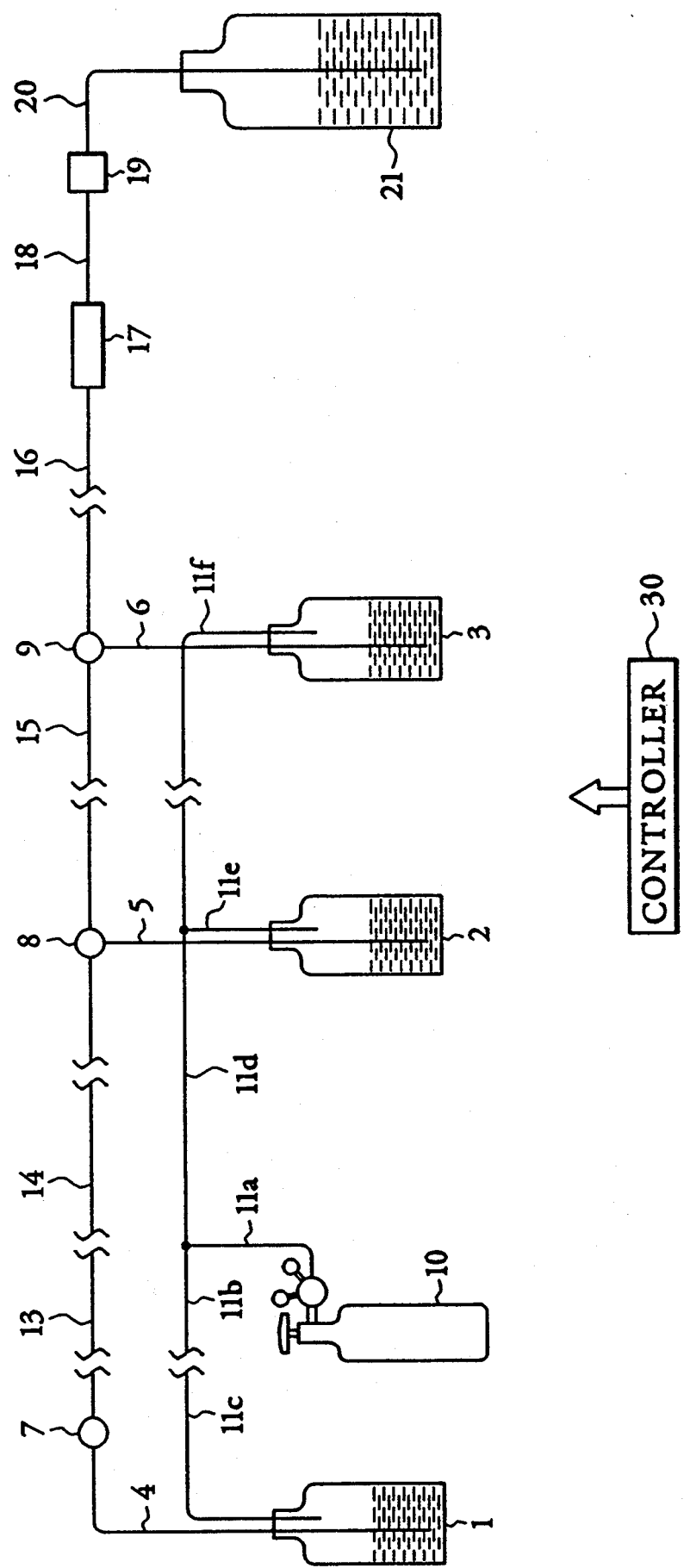
FIG. 1 is a simplified schematic diagram of an automated nucleic acid synthesis instrument.

FIG. 1 illustrates the simplified schematic arrangement of an automated chemical processing apparatus suitable for use to synthesize DNA. This is a simplified fluid diagram for the purpose of illustrating the basic concept of the invention. A fully automated apparatus typically comprises more reagent reservoirs and additional flow components. It is within the knowledge of one skilled in the art to incorporate the necessary reagent reservoirs and flow components to build an automated DNA synthesizing apparatus which incorporates the present invention in light of the disclosure of U.S. Pat. No. 4,458,066 to Caruthers et al which had been incorporated by reference herein.

Referring to FIG. 1, reservoirs 1, 2 and 3 contain appropriate chemical reagents for DNA synthesis, e.g. acetonitrile, tetrazole, oxidizer, different phosphoramidites, capping activator, deblocker, etc. Tubings 4, 5 and 6 have ends immersed in the reagents and are connected to valves 7, 8 and 9 which turn on and off fluid delivery from the reservoirs 1, 2 and 3. The valve 1 is a normally-closed two port valve. When it is actuated, it permits flow from tube 4 to tube 13. When it is released, it blocks flow between tubes 4 and 13. The valves 8 and 9 are normally-closed 3-port 2-way valves. When one of these valves is actuated, all the ports are opened, so that flow may occur in any direction through any port. When the valve is released, only the port connected to the associated reservoir is closed. The valves 7, 8 and 9 may be of the electromechanical type which are actuated under control by controller 30. While the valves are shown to be connected in series, an integrated valve may be implemented to form similar or additional valving functions.

Each reservoir 1, 2 and 3 is capped. Tubes 11a–f deliver a pressurized inert gas such as helium from a tank 10 to above the reagent level in each reservoir. Consequently, when a valve (7, 8, 9) is actuated, the reagent in the reservoir connected to that valve will be forced into the associated supply tube (4, 5, 6) and through the valve by the pressurized gas. Downstream of the valves is a reaction column 17 in accordance with the present invention which contains a solid-phase support designed to facilitate the desired synthesis reactions, in this case synthesis of nucleotides. Further downstream is a detector 19 positioned along or adjacent the flow path 18 to monitor the passing fluid flow. At the very end of the flow system 20, a waste container 21 is provided to collect the spent reagents that have flowed through the system, and/or a collection device (not shown) is provided to collect synthesized oligonucleotide if the cleavage and deprotection steps are also carried out by the instrument. Otherwise, the reaction column 17 may be removed from the instrument for manually implementing the cleavage and deprotection steps. The structure of the reaction column 17 is described in greater detail below.

An actual DNA synthesizing apparatus consists of many more reservoirs and valves than depicted in FIG. 1, but its operation may be adequately described with reference to this simplified fluid system for the purposes of discussing the current invention.

In operation, the reagents in the reservoirs are delivered to the reaction column 17 by actuating one or more of the valves 7, 8, 9 in a desired sequence for the particular chemical reactions desired to take place at the reaction column 17. For example, the valve 7 is actuated to permit the reagent from the reservoir 1 to flow through the tubes 4, 13, 14, 15 and 16 and reaction column 17 followed by actuation of the valve 8 to permit the reagent from the reservoir 2 to flow through the tubes 5, 15 and 16 and enter reaction column 17. A mixture of the reagents may be delivered by actuating two or more of the valves simultaneously. The synchronization of valve actuations as well as other system functions are controlled by a programmable controller 30.

Figure 2:
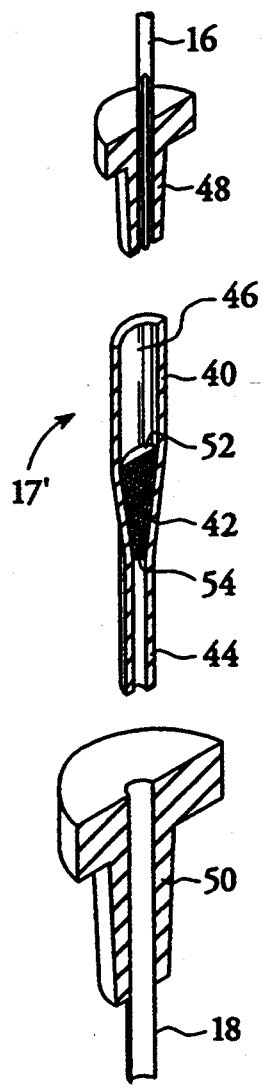
FIG. 2 is a sectional diagram illustrating the structure of a reaction column in accordance with one embodiment of the present invention.

Referring to FIG. 2, a first embodiment of a reaction column in accordance with the present invention is illustrated. The reaction column 17' has a cylindrical column 40 containing a solid-phase support 42. The column is made of a material that is chemically inert to the reagents used in nucleic acid synthesis, e.g. polypropylene. At the other end of the column 40 is a hollow metal needle 44, e.g. a hypodermic needle. The opening 46 of the column 40 is sized to fit the tubing 16 (FIG. 1) in the instrument or an adaptor 48 at the end of the tubing 16 as shown in FIG. 2. The needle 44 is sized to fit into the tubing 18 (FIG. 1) or an adapter 50 at the end of the tubing 18 as shown in FIG. 2. The reaction column 40 may be modified from the dispensing tips (e.g. part no. 5121) supplied by EFD Co. in East Providence, R.I. The solid-phase support 42 can be particulated or gel medium which is made of or treated with a material suitable for nucleic acid synthesis, for example derivitized controlled pore glass manufactured by CPG, Inc. The support 42 is maintained in position within the column 40 by frits 52 and 54 or other screen materials which allow fluid flow therethrough. A suitable screen may be a polypropylene screen having a 160×160 mesh per square inch with an open area of 22% (part no. 9275T26 available from McMaster-Carr Supply Co. in Los Angeles, Calif.). The reaction column 17 can be easily removed from the instrument by simply unplugging the column 17' from the adapters 48 and 50.

Figure 3B:
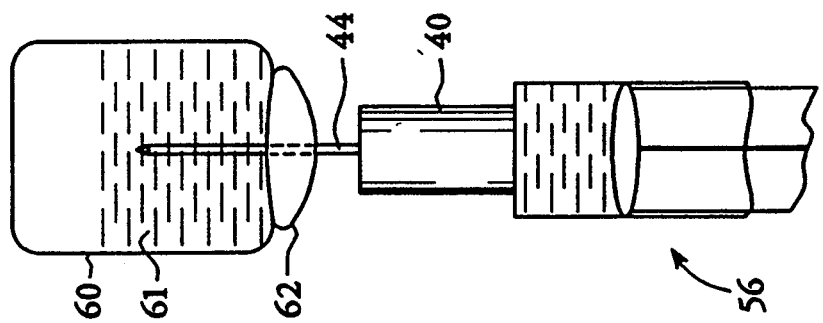
FIG. 3A–C illustrate the steps for cleavage and deprotection using the reaction column of FIG. 2.
Figure 3A:
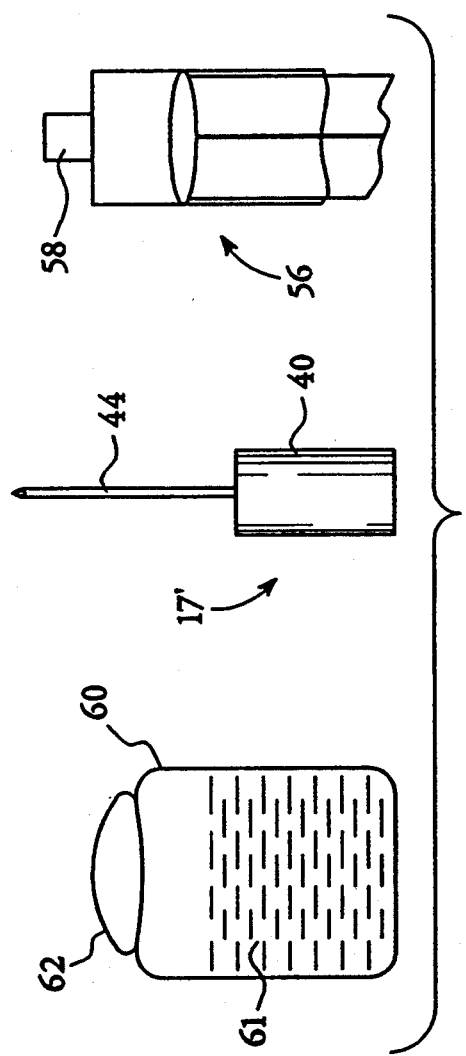
Figure 3C:
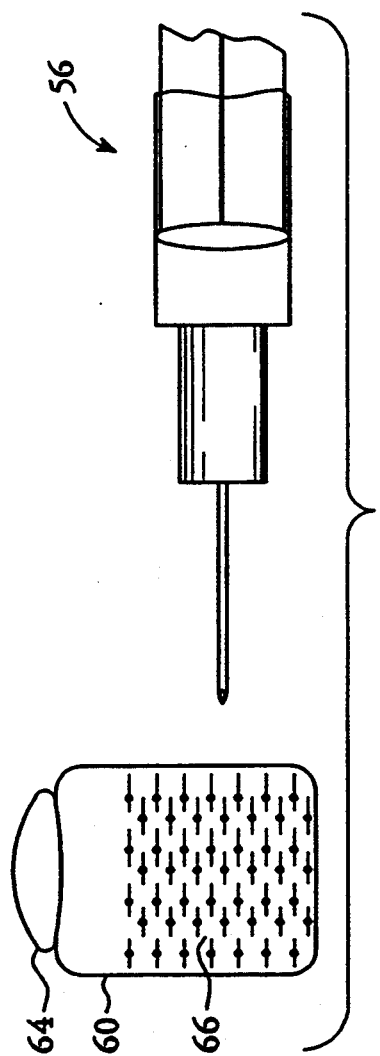

Referring to FIGS. 3A–C, the manual steps of cleavaging and deprotecting synthesized oligonucleotide which is bound to the solid-phase support in the reaction column are illustrated. In step 1, the reaction column 17' has already been removed from the instrument, a disposable syringe 56 having a tip 58 that will interference fit into the opening 46 of the column 40 is provided, and a cleavage and deprotection reagent 61 such as concentrated ammonia solution in a septum sealed vial 60 is provided. The syringe is available from Becton Dickinson & Co. in Rutherford, N.J., U.S.A. (part no. 9625). In Step 2, the column 40 is fitted onto the tip of the syringe 56, the metal needle 44 is forced to puncture the septum 62, and the reagent 61 is withdrawn from the vial 60 in sufficient quantity to flood the reaction column and saturate the support bound oligonucleotide. The reagent may be forced back and forth across the reaction column several times by action of the syringe to loosen air pockets trapped in the solid-phase support so as to ensure that the column is fully saturated with reagent. The assembly as shown in FIG. 3B is essentially a sealed unit in which cleavage process takes place for one hour. In step 3, the reagent 66 containing the cleaved oligonucleotide is ejected from the column 40 into the vial, the punctured septum is replaced with a fresh septum 64 and the vial is heated to 70° C. for 90 minutes to complete the removal of the protecting groups on the oligonucleotide. The deprotected oligonucleotide may be extracted from the bulk of the reagent by "filtering" or evaporating the reagent. The syringe 56 and reaction column 17' may be discarded.

It can be seen that the foregoing cleavage and deprotection steps can be conveniently carried out using one syringe, one reagent vial and the reaction column, without having to use adapters for connecting reagent vials to the reaction column as is the case in prior art processes. It is noted that the chemistry and conditions for cleavage and deprotection are not the subject matter of the present invention and they can follow those utilized in conventional implementations. Rather, the present invention is directed to the novel configuration of the reaction column and the methodology for post synthesis sample manipulation implementing the reaction column.

While a manual approach in cleavage and deprotection process has been disclosed, the process may be automated by the instrument after synthesis. Appropriate cleavage and deprotection reagents may be delivered to the reaction column by the fluid delivery system illustrated in FIG. 1. The cleavage and deprotection process may also be automated by a dedicated device supplied with the appropriate reagents.

Figure 4:
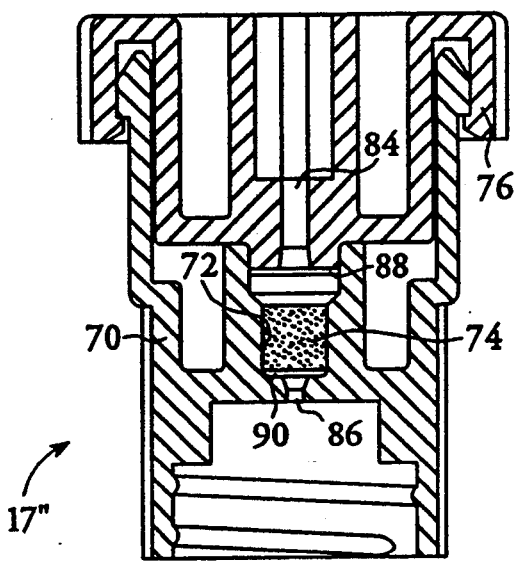
FIG. 4 is a sectional diagram illustrating the structure of a reaction column in accordance with another embodiment of the present invention.
Figure 5:
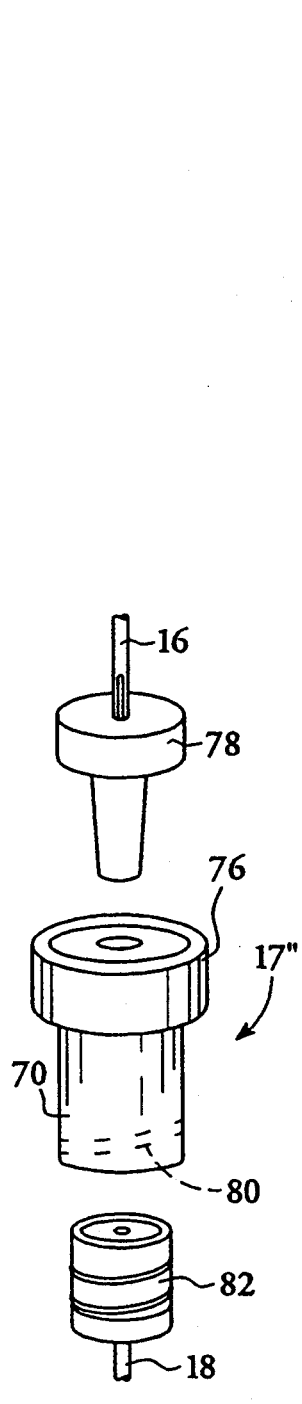
FIG. 5 illustrates the connection of the reaction column of FIG. 4 to the flow system.

Another embodiment of a synthesis reaction column 17" according to the present invention is illustrated by FIG. 4. The reaction column 17" has a cylindrical barrel 70 defining a reaction chamber 72 which encloses the solid-phase support 74. Referring also to FIG. 5, one end of the barrel 70 has a cap 76 which is adapted to receive the end of tubing 16 or an adapter 78 on the end of the tubing 16 (FIG. 1). The barrel 70 has at the other end a female-threaded extension 80 adapted for receiving a complementary male-threaded adapter 82 on the end of the tubing 18 (FIG. 1). It is understood that the adapter 82 may instead be female-threaded and the extension 80 male-threaded. Through-holes 84 and 86 are provided in the cap 76 and at the extension end 80 of the barrel 70 to allow fluid flow through the barrel across the solid-phase support 74. Mesh screens 88 and 90 are positioned (plastic welded) across the through-holes 84 and 86 to retain the solid-phase support 74. The solid-phase support 74 has been derivitized to anchor a nucleotide ("A", "C", "T" or "G") as the starting block for synthesis. The actual size and configuration of the reaction chamber 72 depend on the synthesis scale. The reaction column shown in FIG. 4 (approximately to scale; the barrel 70 has overall dimensions of approximately 1 inch length and 0.6 inch diameter) is suitable for use to synthesize up to 200 nMole of oligonucleotide. The barrel 70 and the cap 76 may be separate parts molded from an inert polymer such as polypropylene, the parts being press-fitted or welded together upon assembly. It can be seen that the reaction column 17" can be easily removed from the flow system illustrated in FIG. 1 by simply unplugging the adapter 78 and unscrewing the barrel 70 from the adapter 82.

Figure 6:
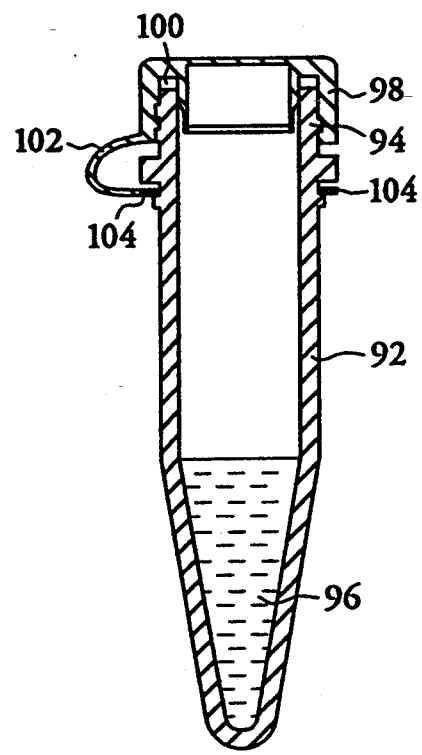
FIG. 6 is a sectional diagram illustrating the vial utilized for cleavage and deprotection procedure.

Referring to FIG. 6, a vial 92 having a male-threaded neck 94 is utilized to contain the cleavage/deprotection reagent 96. The vial has a female-threaded cap 98 having an O-ring 100 for sealing when the cap 98 is threaded onto the neck 94. For convenience, the cap 98 is mounted to the base of the threaded neck 94 via a strip 102 and a ring 104 which is rotatable about the neck 94. This vial 92 is supplied by Sarstedt, Inc. in Hayward, Calif., U.S.A. (part no. 72.692.100).

Figure 7A:
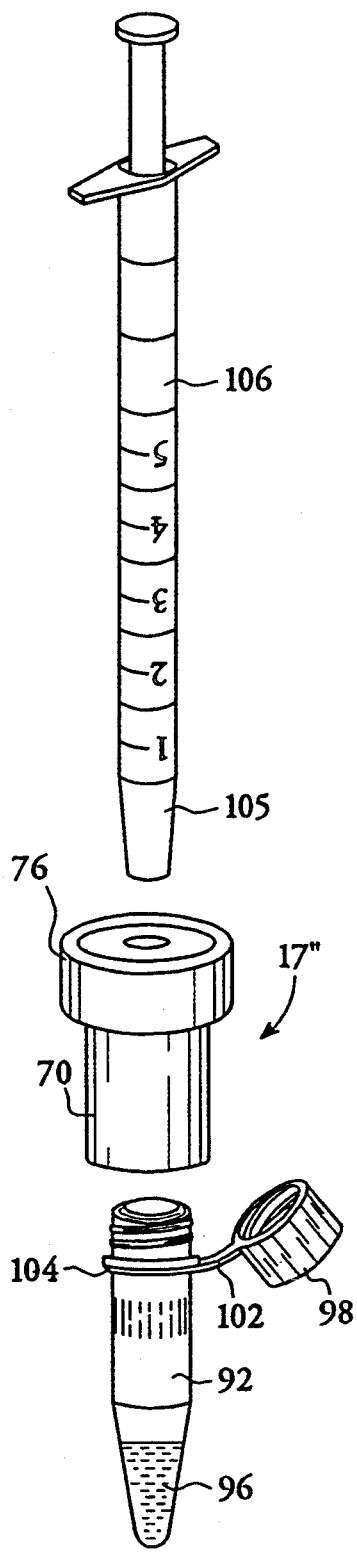
FIGS. 7A and B illustrate the use of the reaction column of FIG. 4 in combination with a reagent vial that threads to one end of the reaction column.
Figure 7B:
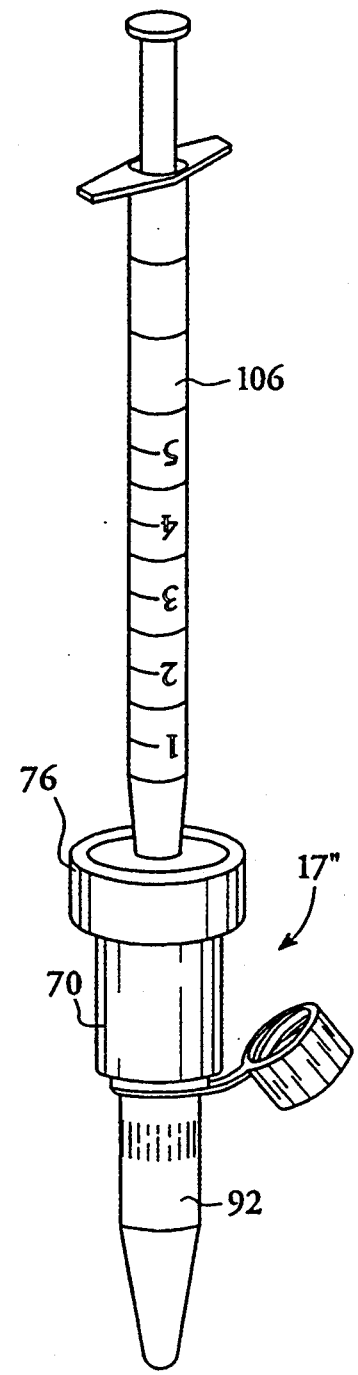

Referring to FIGS. 7 A and B, the cleavage and deprotection procedure using the vial 92 and threaded column 17" is described. After removing the reaction column containing solid bound oligonucleotide from the flow system, the vial 92 containing the cleavage/deprotection reagent 96 is threaded to the threaded end of the barrel 70. The tip 105 of a disposable syringe 106 is fitted into the cap 76. The assembly of the various parts are shown in FIG. 7B. The reagent 96 is withdrawn from the vial in sufficient quantity to flood the reaction column and saturate the support bound oligonucleotide. The reagent may be forced back and forth across the reaction column several times by action of the syringe to loosen air pockets trapped in the solid-phase support so as to ensure that the column is fully saturated with reagent. The assembly as shown in FIG. 7B is essentially a sealed unit in which cleavage process takes place. After about one hour, or after cleavage of the solid bound oligonucleotide has been completed, the reagent containing the cleaved oligonucleotide is ejected from the column into the vial. The vial is capped and is heated to 70° C. for 90 minutes to complete the removal of the protecting groups on the oligonucleotide. The deprotected oligonucleotide may be extracted from the bulk of the reagent by filtering or evaporating the reagent. The syringe 106 and reaction column 17" may be discarded.

It can be seen that, as in the case of the previous embodiment, the foregoing cleavage and deprotection steps can be conveniently implemented using one syringe and the reaction column, without having to use adapters for connecting reagent vials to the reaction column as is the case in the prior art processes. Like the previous embodiment, this threaded reaction column can be used to implement automated on-line cleavage and deprotection.

The syringe 106 and the threaded vial 92 containing reagent 96 may be packaged as a cleavage and deprotection kit for the convenience of the user.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific illustrated embodiment, but only by the scope of the appended claims.

We claim:
1. A synthesis reaction assembly comprising:
    a cylindrical chamber having a first diameter, a first end having an opening with a second diameter, a second end having an orifice opposite said opening, said orifice having a third diameter,
    a solid-phase synthesis support positioned within said chamber,
    a first means, resting between said opening and said support, for retaining said support within said chamber while maintaining constant fluid communication through said opening,
    a second means, resting between said orifice and said support, for retaining said support within said chamber while maintaining constant fluid communication through said orifice, with said solid-phase synthesis support being suitable for nucleic acid synthesis, and said first end being tapered so that said first diameter is substantially larger than said second diameter and said third diameter being at least as large as said first diameter.

2. The synthesis reaction assembly as recited in claim 1 further including a cap being slidably received in said orifice for forming an interference fit with said chamber, wherein said cap includes a top portion with a first aperture, a lower portion with a second aperture, and a passageway extending therebetween, said second aperture being proximate to said second retaining means when said cap is in a final seating position.

3. The synthesis reaction assembly as recited in claim 2 including a syringe with a cylindrical tip having a diameter proximate to said first aperture and slidably received therein for forming an interference fit with said cap.

4. The synthesis reaction assembly as recited in claim 2 with said chamber having an upper portion, the outer side of said upper portion having a first annular ridge, said cap having an inwardly extending annular ridge complementary to said first annular ridge for interlocking therewith, securely attaching said cap to said upper portion.

5. The synthesis reaction assembly as recited in claim 2 wherein said top portion includes an annular flange concentric about said passageway, said lower portion comprising a cylindrical protrusion having a diameter proximate to said orifice and slidably received therein to form an interference fit with said chamber, the terminus of said protrusion resting proximate to said second retaining means upon said cap reaching the final seating position.

6. The synthesis reaction assembly as recited in claim 2 wherein said tapered end has a hollow needle rigidly attached thereto and extending outwardly therefrom, said needle having a piercing tip for puncturing a septum of a sealed container, with said tip maintaining constant fluid communication with said first aperture.

7. The synthesis reaction assembly as recited in claim 1 further including a second cylindrical chamber integrally formed with, and positioned adjacent to, said chamber with said first end being in constant fluid communication therewith, said second chamber having a threaded lower portion terminating in a second opening.

8. The synthesis reaction assembly as recited in claim 7 wherein said passageway, located proximate to said second aperture, flares outward towards said chamber, defining a flared end, and said second retaining means being rigidly attached to said flared end, said first retaining means being rigidly attached to said tapered end.

9. The synthesis reaction assembly as recited in claim 7 further including a cylindrical vial having a threaded neck received in said threaded lower portion.

10. The synthesis reaction assembly as recited in claim 1 further including a syringe with a cylindrical tip having a diameter proximate to said orifice and slidably received therein for forming an interference fit therewith.

11. A synthesis reaction assembly comprising:
    a cylindrical chamber with a first end having an opening and a second end having an orifice opposite said opening,
    a solid-phase synthesis support positioned within said chamber,
    a first means, resting between said opening and said support, for retaining said support within said chamber while maintaining constant fluid communication through said opening,
    a second means, resting between said orifice and said support, for retaining said support within said chamber while maintaining constant fluid communication through said orifice, with said solid-phase synthesis support being suitable for nucleic acid synthesis, and
    a cap slidably received in said orifice for forming an interference fit with said chamber, wherein said cap includes a top portion with a first aperture, a lower portion with a second aperture, and a passageway extending therebetween, said lower portion comprising a cylindrical protrusion having a diameter proximate to said orifice to form an interference fit with said chamber, the terminus of said protrusion resting proximate to said second retaining means to hold said support between said first retaining means and said second retaining means, upon said cap reaching a final seating position.

12. The synthesis reaction assembly as recited in claim 11 with said chamber having an upper portion, the outer side of said upper portion having a first annular ridge, said cap having an inwardly extending annular ridge complementary to said first annular ridge for interlocking therewith, securely attaching said cap to said upper portion.

13. The synthesis reaction assembly as recited in claim 12 including a syringe with a cylindrical tip having a diameter proximate said first aperture and received therein for forming an interference fit with said cap.

14. The synthesis reaction assembly as recited in claim 13 further including a second cylindrical chamber integrally formed with, and positioned adjacent to, said chamber with said tapered end being in constant fluid communication therewith, said second chamber having a threaded lower portion terminating in a second opening with a cylindrical vial having a threaded neck received in said threaded lower portion.

15. A synthesis reaction assembly comprising:
    a cylindrical chamber having a first diameter, a first end having an opening with a second diameter, a second end having an orifice opposite said opening, said orifice having a third diameter, a body being cylindrical, having an upper portion above said chamber, the outer side of said upper portion having a first annular ridge for interlocking with a cap, a solid-phase synthesis support positioned within said chamber, a first means, resting between said opening and said support, for retaining said support within said chamber while maintaining constant fluid communication through said opening, a second means, resting between said orifice and said support, for retaining said support within said chamber while maintaining constant fluid communication through said orifice, with said solid-phase synthesis support being suitable for nucleic acid synthesis, and said first end being tapered so that said first diameter is substantially larger than said second diameter with said third diameter being at least as large as said first diameter, a cap slidably received in said orifice for forming an interference fit with said chamber, wherein said cap includes a top portion with a first aperture, a lower portion with a second aperture, and a passageway extending therebetween, said lower portion comprising a cylindrical protrusion having a diameter proximate to said orifice to form an interference fit with said chamber, the terminus of said protrusion resting against said second retaining means to wedge said support between said first retaining means and said second retaining means, upon said cap reaching a final seating position, said cap having an inwardly extending annular ridge complementary to said first annular ridge for interlocking therewith, securely attaching said cap to said body.

16. The synthesis reaction assembly as recited in claim 15 wherein said body has integrally formed thereto a second chamber positioned adjacent to said chamber with said tapered end being in constant fluid communication therewith, said second chamber having a threaded lower portion terminating in a second opening.

17. The synthesis reaction assembly as recited in claim 16 further including a cylindrical vial having a threaded neck received in said threaded lower portion.

* * * * *